(12) United States Patent
Kim et al.

(10) Patent No.: US 7,182,737 B2
(45) Date of Patent: Feb. 27, 2007

(54) APPARATUS AND METHOD FOR MEASURING JAW MOTION

(75) Inventors: Mun-sang Kim, Seoul (KR); Joong-han Kim, Seoul (KR)

(73) Assignee: Korea Institute of Science & Technology, Seoul (KR)

( * ) Notice: Subject to any disclaimer, the term of this patent is extended or adjusted under 35 U.S.C. 154(b) by 557 days.

(21) Appl. No.: 10/644,796

(22) Filed: Aug. 21, 2003

(65) Prior Publication Data
US 2005/0075585 A1   Apr. 7, 2005

(30) Foreign Application Priority Data
Aug. 26, 2002   (KR) .................. 10-2002-0050544

(51) Int. Cl.
*A61B 5/103* (2006.01)
*A61B 5/117* (2006.01)

(52) U.S. Cl. ...................... 600/590; 600/587
(58) Field of Classification Search ............... 600/587, 600/590, 595; 433/68–69
See application file for complete search history.

(56) References Cited

U.S. PATENT DOCUMENTS

| | | | | |
|---|---|---|---|---|
| 3,662,535 A | * | 5/1972 | Hedrick et al. ............. | 368/112 |
| 4,813,436 A | * | 3/1989 | Au ............................. | 600/592 |
| 4,836,778 A | | 6/1989 | Baumrind et al. | |
| 5,143,086 A | * | 9/1992 | Duret et al. ................ | 600/590 |
| 5,340,390 A | | 8/1994 | Magauran et al. | |
| 5,459,793 A | * | 10/1995 | Naoi et al. .................. | 382/165 |
| 6,120,290 A | * | 9/2000 | Fukushima et al. .......... | 433/69 |
| 6,179,612 B1 | * | 1/2001 | Reusch et al. ............... | 433/76 |
| 6,554,706 B2 | * | 4/2003 | Kim et al. .................... | 463/36 |
| 2002/0019258 A1 | * | 2/2002 | Kim et al. .................... | 463/36 |

FOREIGN PATENT DOCUMENTS

KR   KO 0000-61600 A   10/2000

* cited by examiner

*Primary Examiner*—Max Hindenburg
*Assistant Examiner*—H. Q. Nguyen
(74) *Attorney, Agent, or Firm*—Dickstein Shapiro LLP

(57) ABSTRACT

An apparatus for measuring jaw motion has a pair of fixed marker attached to both sides of face of patient, a pair of movable markers disposed to face the fixed marker in a spaced distance and to move in unison with the movement of the lower jaw of patient, four cameras recording the three-dimensional movement of the movable marker relative to the fixed marker, as lower jaw moves, and personal computer for receiving and processing the image signals fed from connected cameras. The apparatus can accurately measure the location of the center of patient's jaw motion and the moving track thereof with stereo vision processing of the image signals obtained from camera.

14 Claims, 12 Drawing Sheets

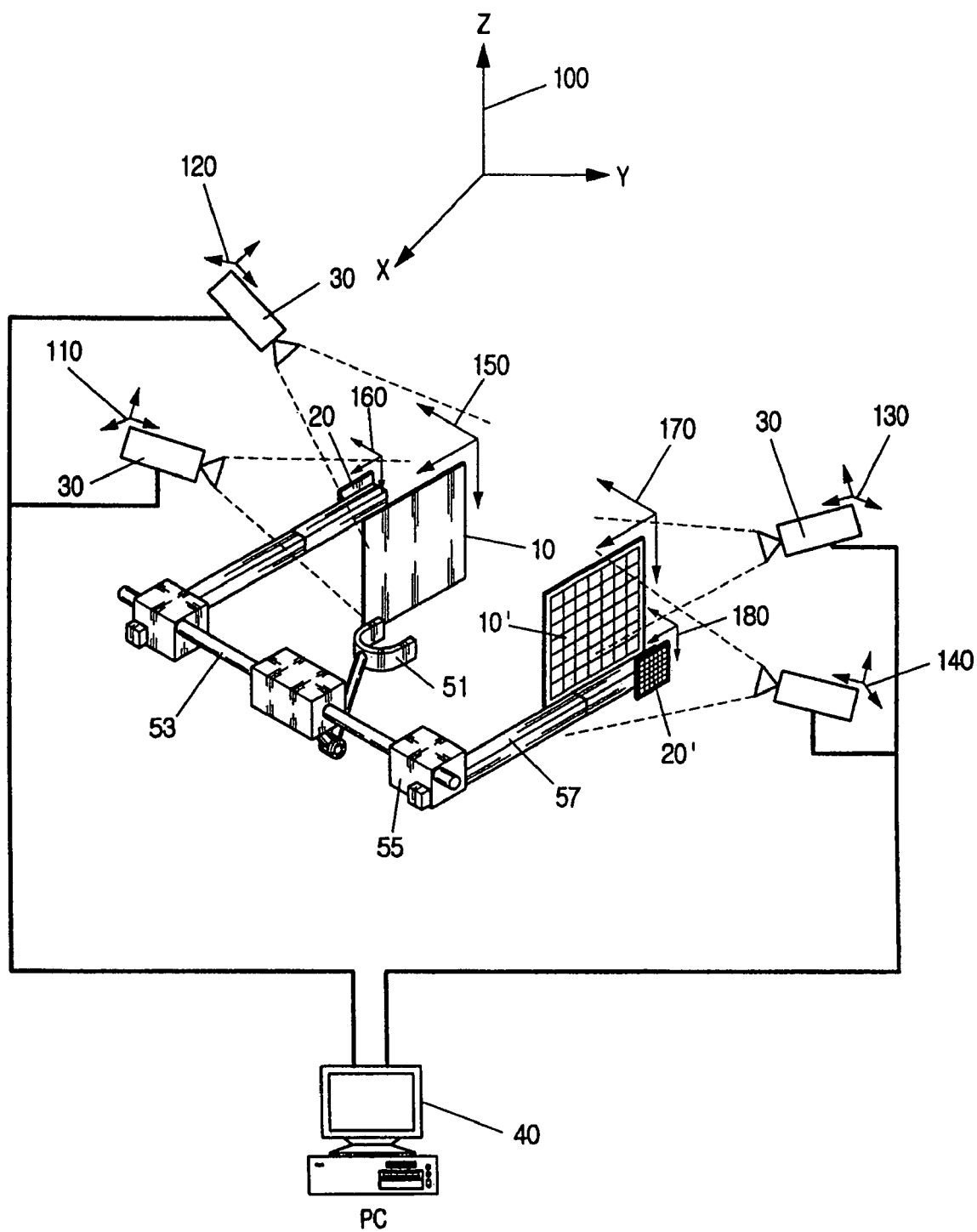
<Fig. 1>

<Fig. 2>
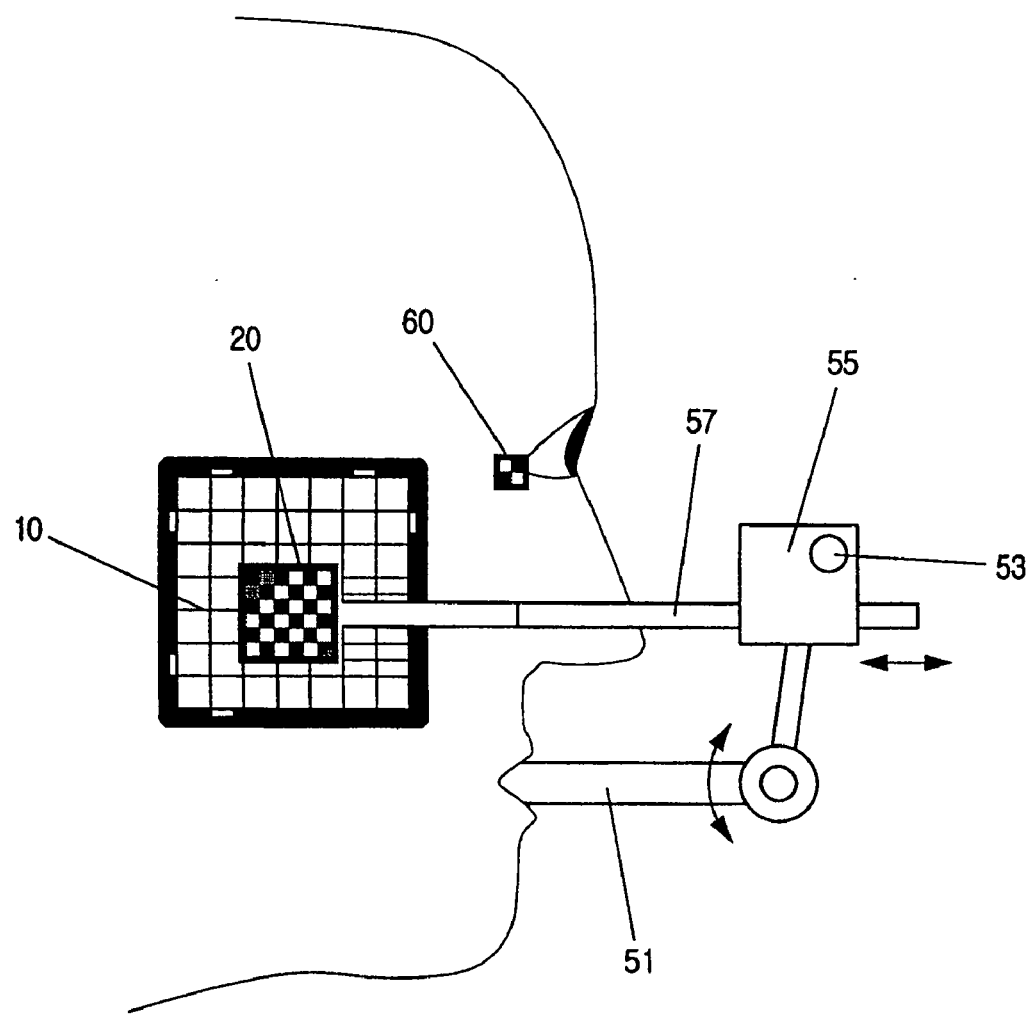

<Fig. 3>
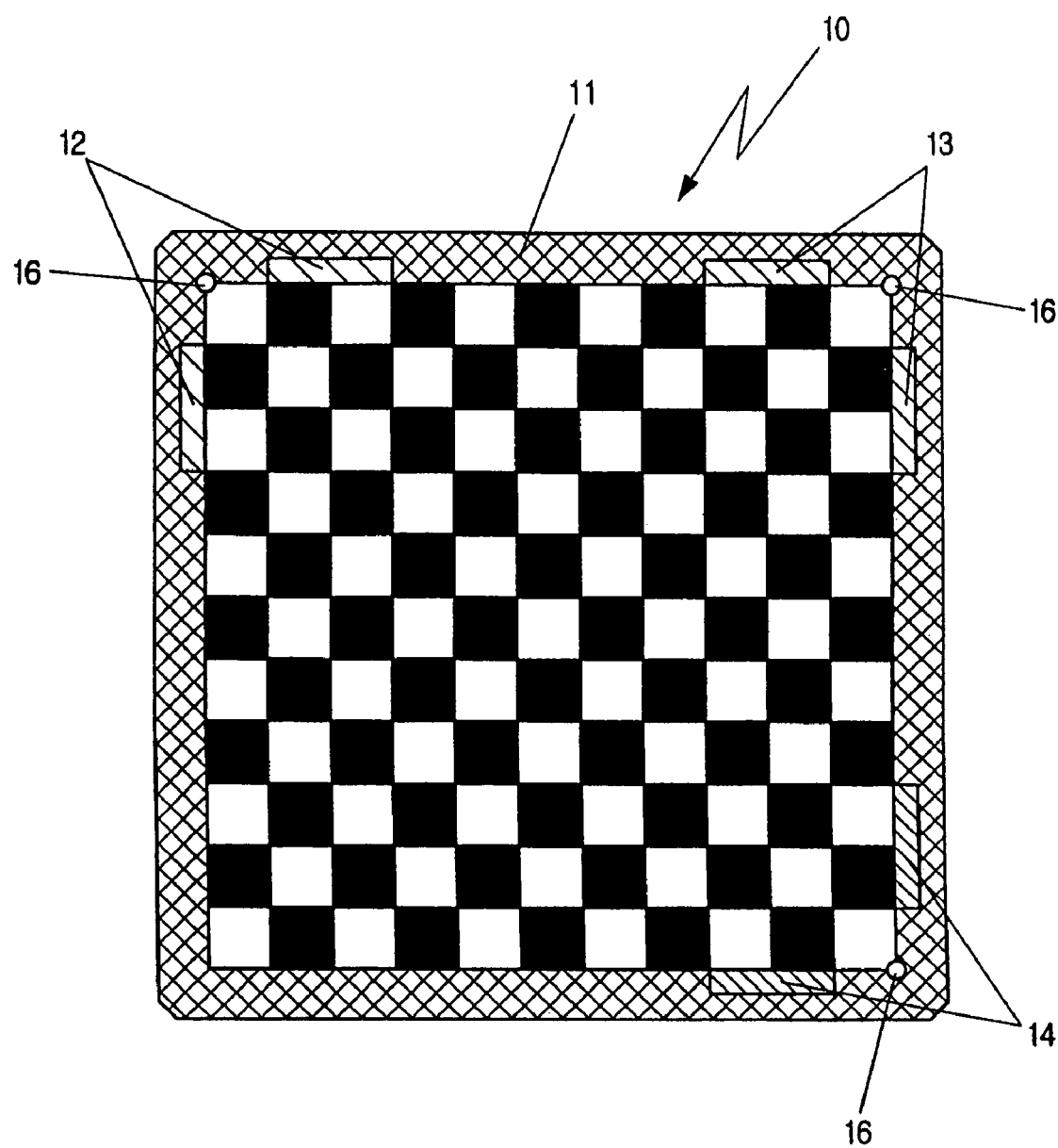

<Fig. 4>
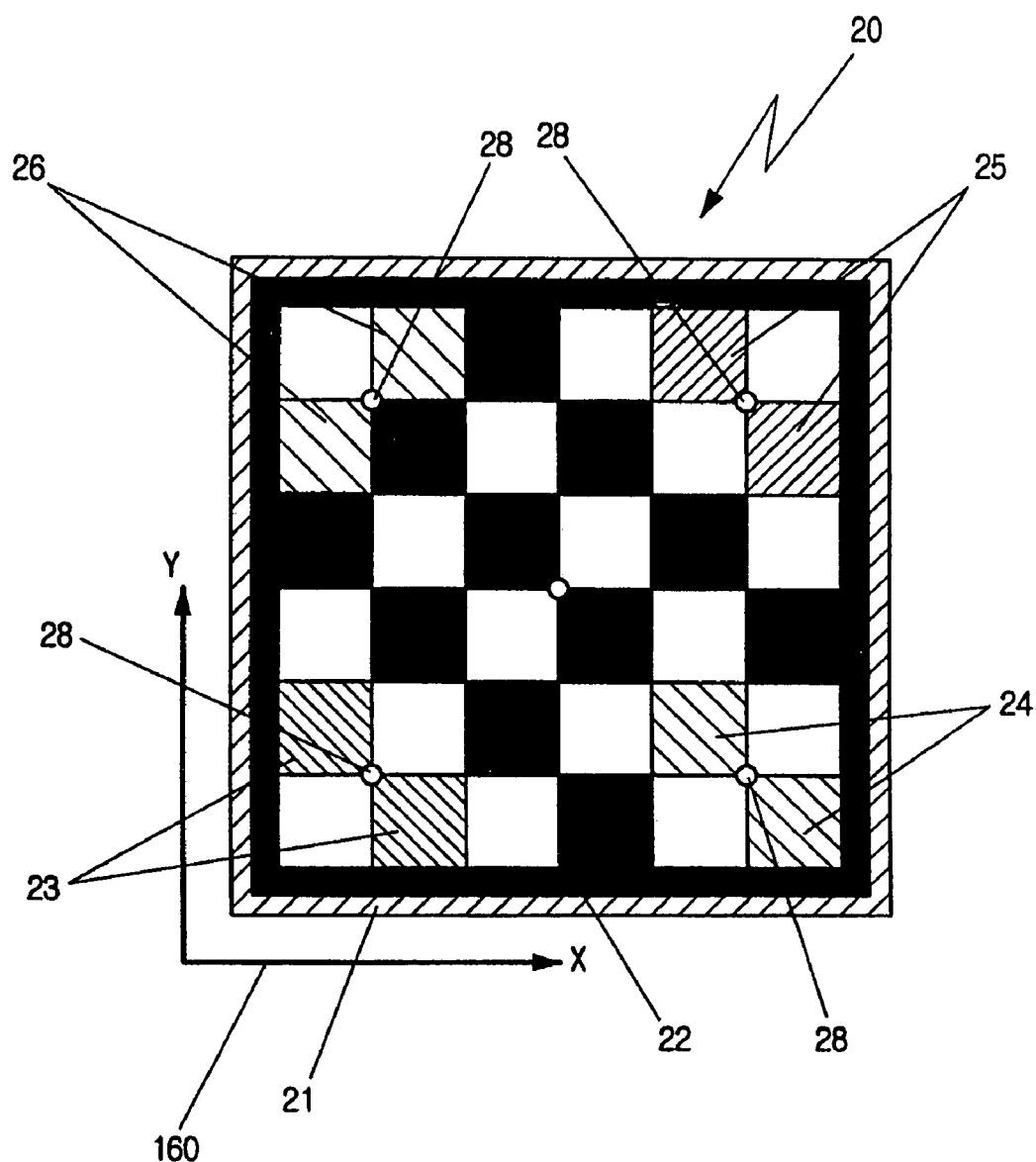

<Fig. 5>
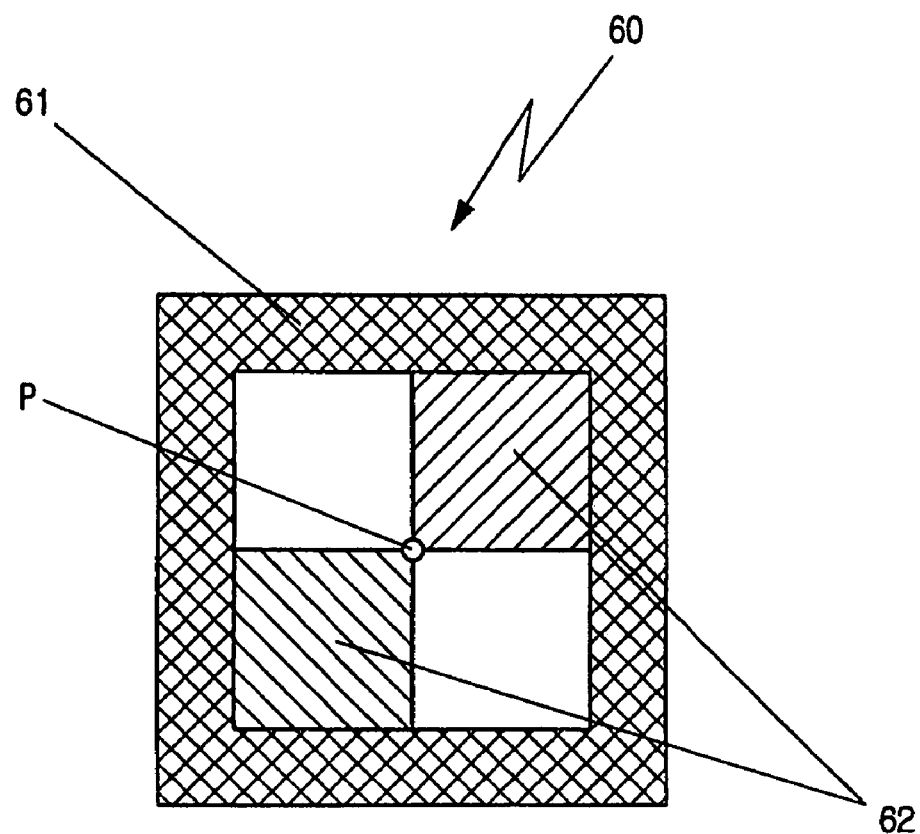

<Fig. 6>
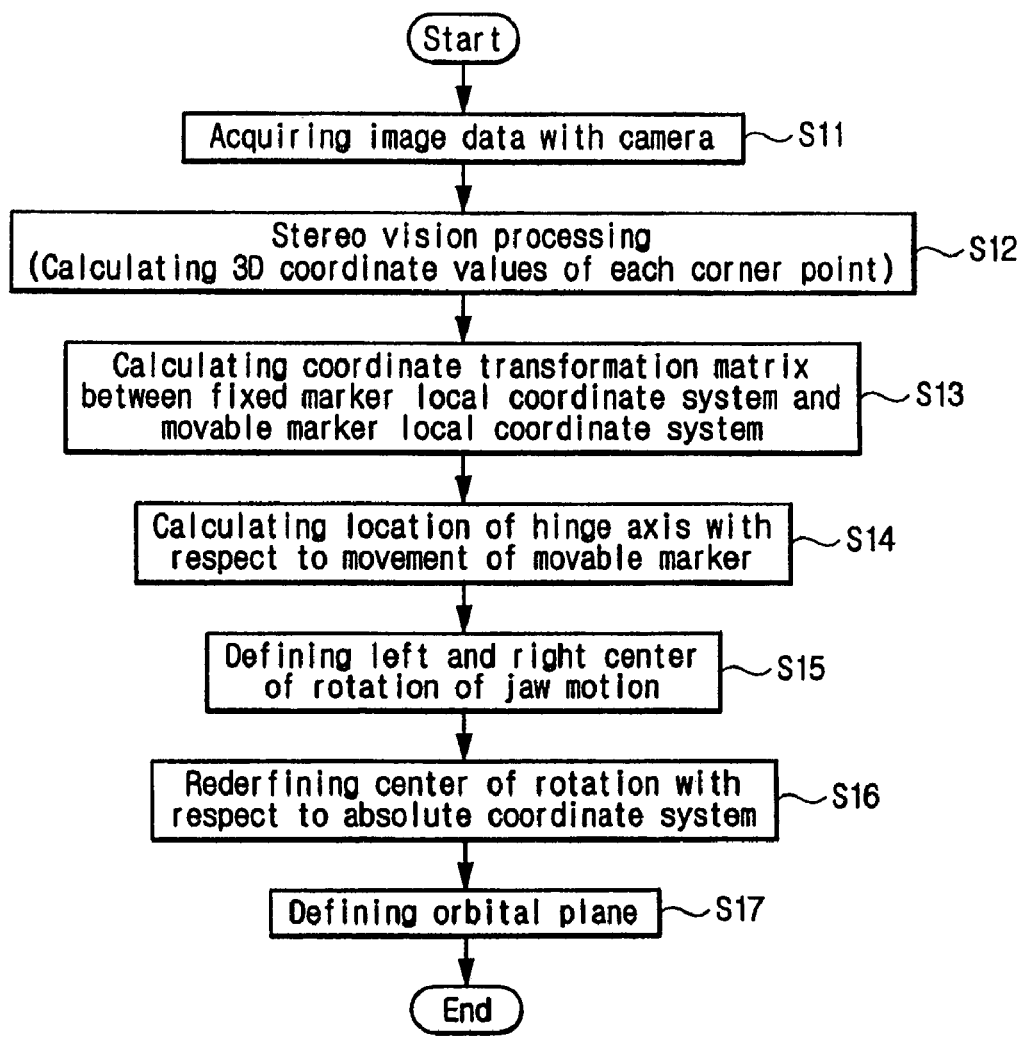

<Fig. 7>
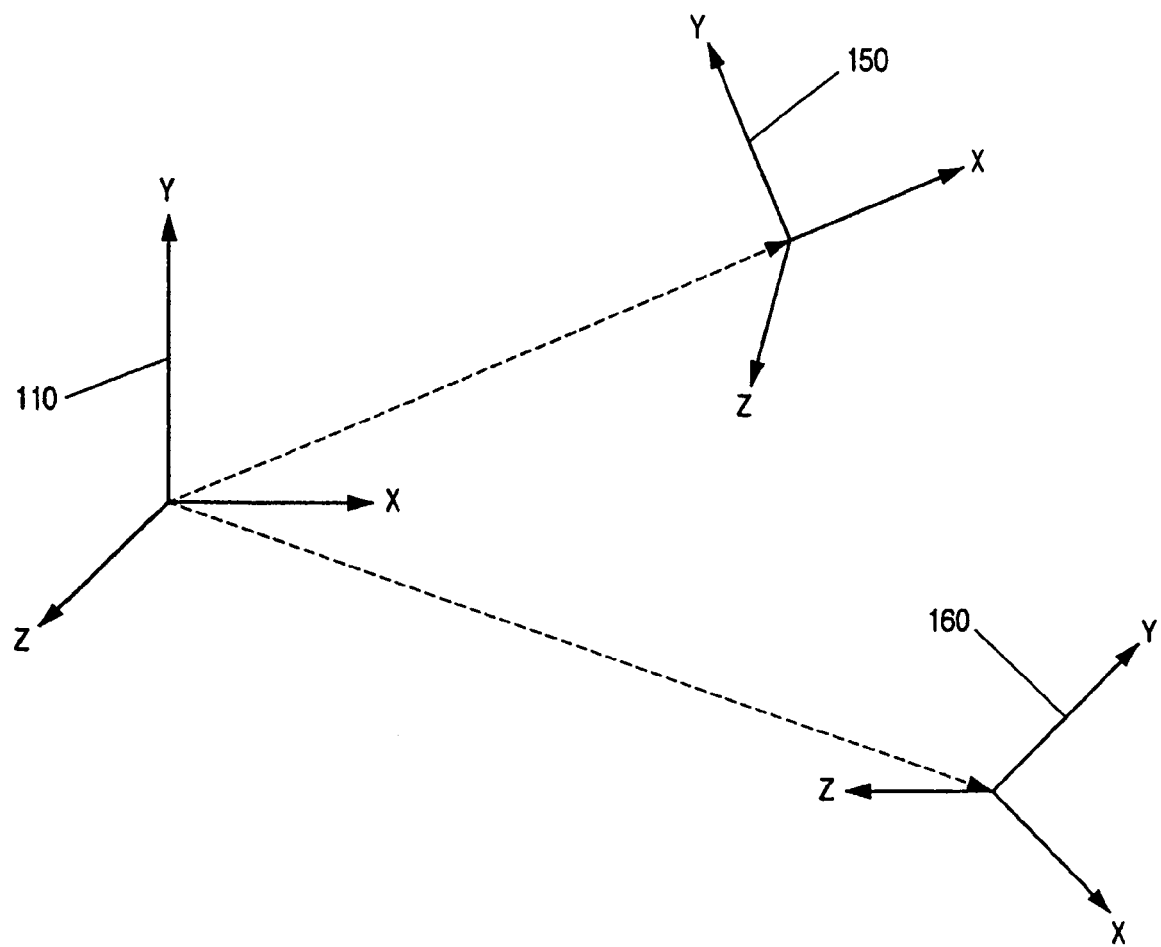

<Fig. 8>
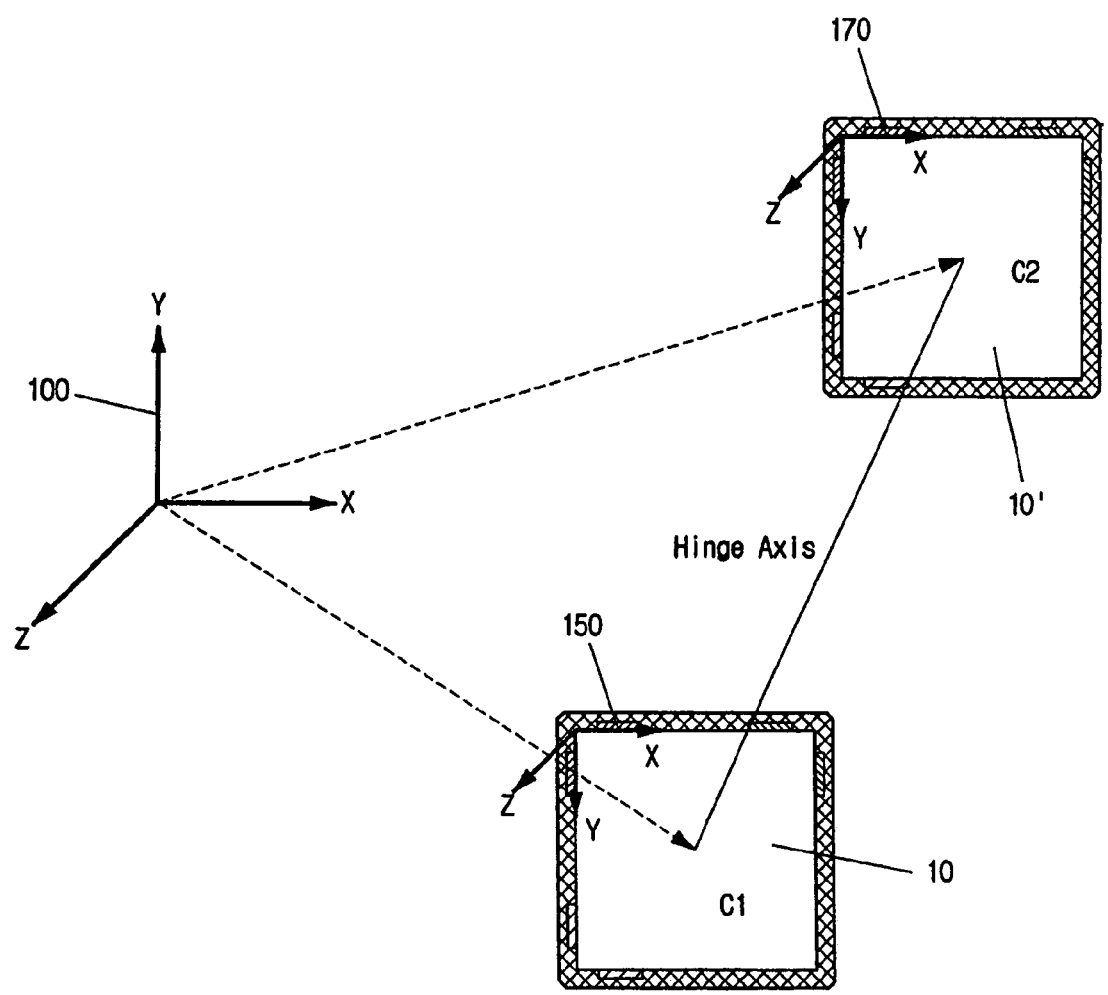

<Fig. 9>
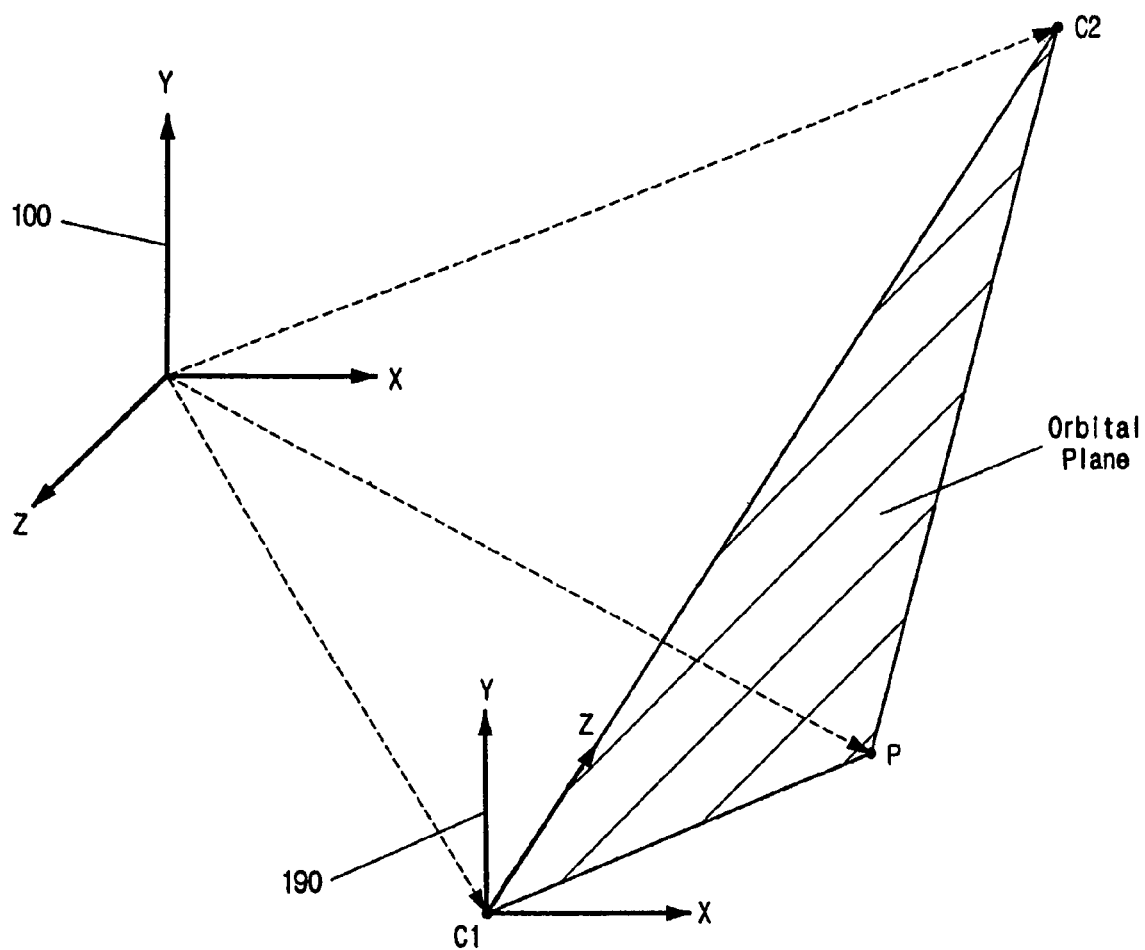

<Fig. 10>
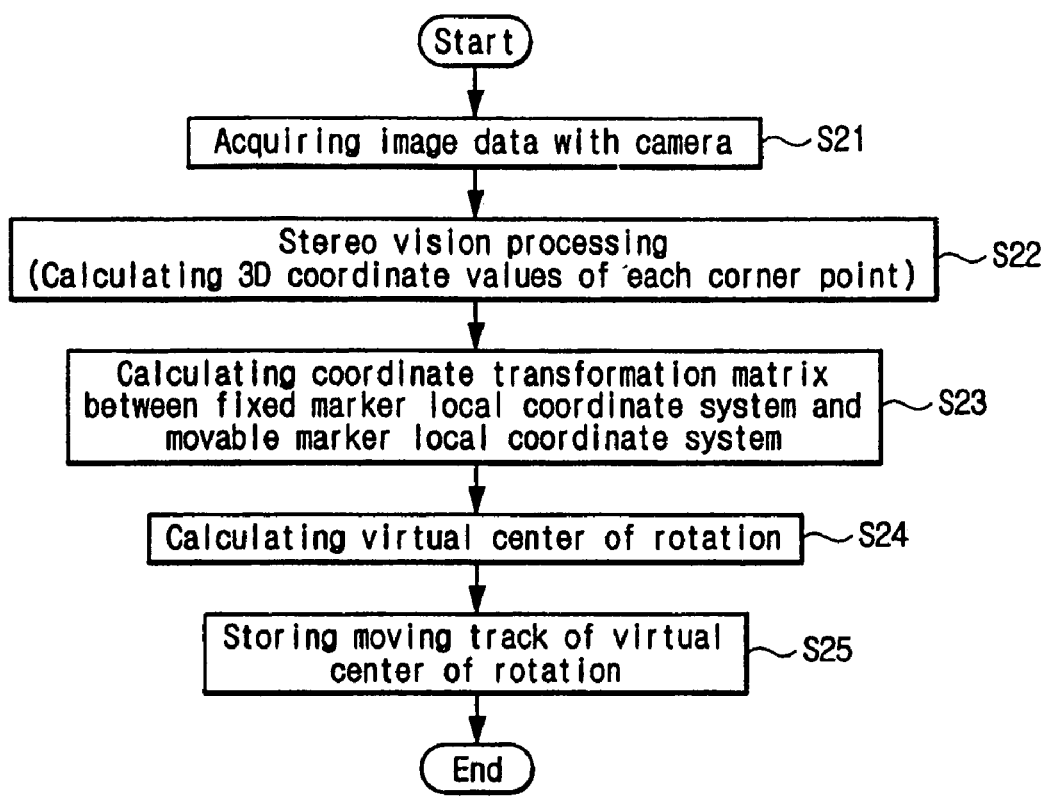

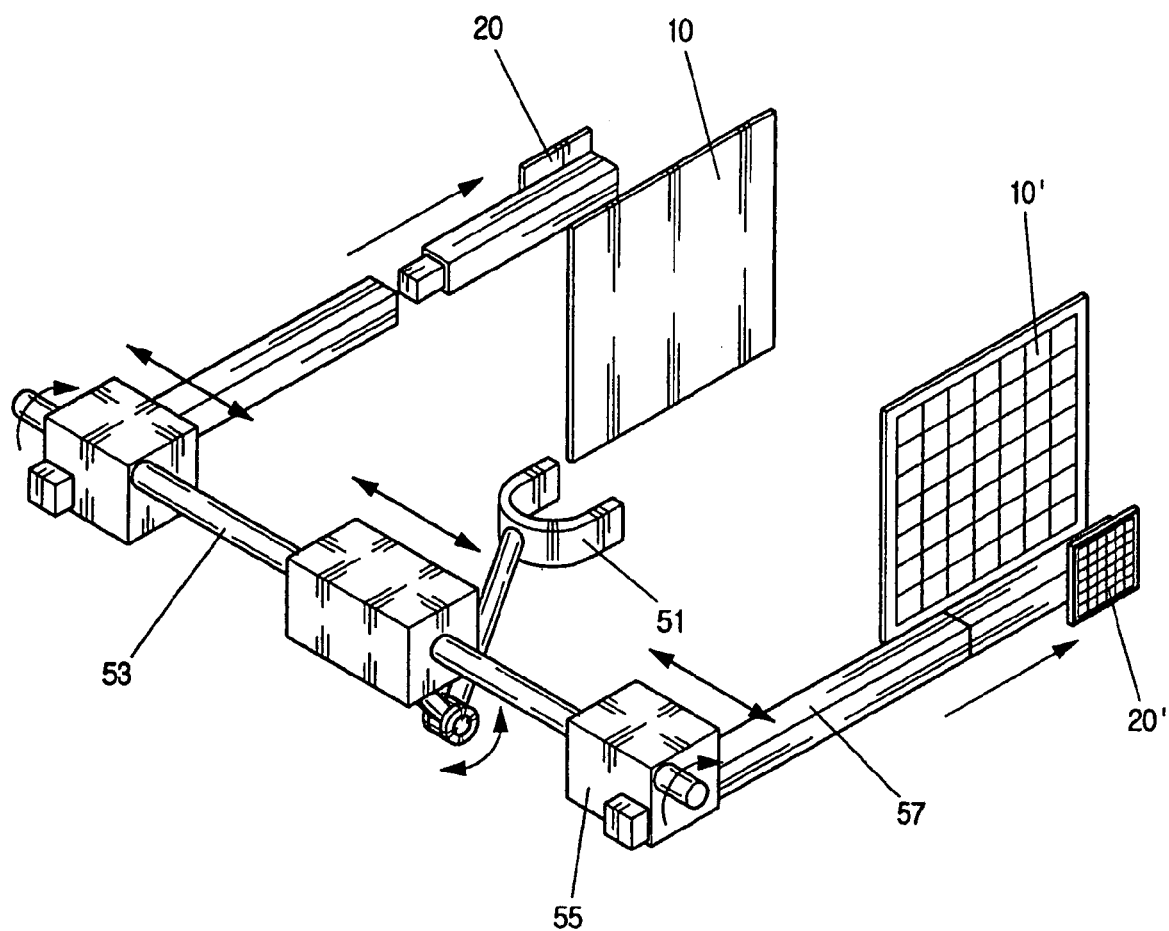
<Fig. 11A>

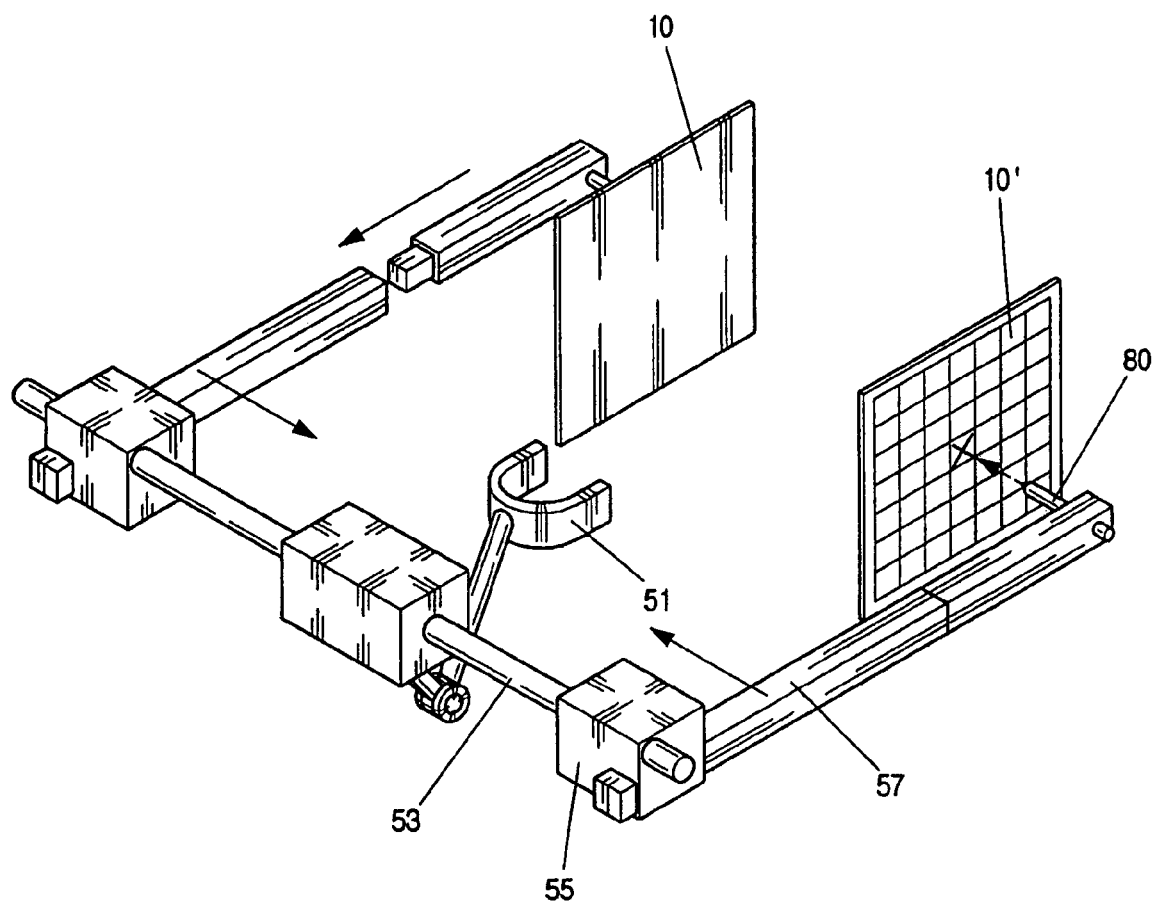
<Fig. 11B>

APPARATUS AND METHOD FOR MEASURING JAW MOTION

CROSS-REFERENCE TO RELATED APPLICATIONS

This application claims the benefit of Korean Patent Application No. 2002-50544, filed on Aug. 26, 2003, in the Korean Intellectual Property Office, the disclosure of which is incorporated herein by reference.

BACKGROUND OF THE INVENTION

1. Field of the Invention

The present invention relates to an apparatus for measuring the motion of jaw for the diagnosis of dental occlusion, and more practically, it relates to a jaw motion measuring apparatus which is short in measuring time and good at the degree of reproducibility.

2. Description of the Prior Art

The analysis of jaw motion is a fundamental element in the field of reconstruction of jaw occlusion and dental treatment of jaw or teeth. In this field, hand-operated apparatus was used to measure the motion of jaw and to analyze and reproduce it. But, this hand-operated apparatus has defects of long measuring time, which conflicts both patients and doctor all together, and the degree of reproducibility was unreliable. In addition, hand-operated apparatus is incapable of producing the adequate data for the diagnosis and treatment of jaw occlusion using CAD, which is in under condense research.

Nowadays the need for automated measuring apparatus is increasing, triggering a series of attempt for developing new automatic measuring apparatus and commercializing it. Those commercialized are using rotation sensor, magnetic sensor, infrared sensor or camera. Among these commercialized, the one using magnetic sensor made a relative success at market. But it is pretty expensive than the hand-operated apparatus, and has difficulties in defining the orbital plane, which is a important concept in the construction of prosthetic devices. Meanwhile, the measuring apparatus using cameras are under research, most of which are based on the Stereo Vision Processing technology employing marker, but was not commercialized yet.

U.S. Pat. No. 4,836,778 and U.S. Pat. No. 5,340,390 disclose the apparatus using camera, but those inventions made no reference to the substantial dental occlusion and treatment, thus lacking practicality.

Especially, dental occlusion simulation system, which uses CAD technology, is under dynamic research, and such simulation system requires low-priced and automated jaw motion measuring apparatus.

SUMMARY OF THE INVENTION

The present invention was devised to solve above the problems of the prior art, and has the purpose of producing a appropriate apparatus for measuring the jaw motion which has a shortened period of measuring time, excellent degree of reproducibility, and applicability to CAD technology.

The other object of present invention is to provide a jaw motion measuring apparatus that can directly mark the center of the motion of jaw, thus being applicable to the conventional diagnosis of occlusion and dental treatment using occlusion device and plaster.

The object of present invention can be achieved by jaw motion measuring apparatus comprising a pair of fixed marker attached to both sides of face of patient; a pair of movable marker disposed to face the fixed marker in a spaced distance and to move in unison with the movement of the lower jaw of patient; a coupling device for connecting the movable marker to the lower jaw of patient; plurality of cameras recording the relative movement of the movable marker in relation to the fixed marker, as lower jaw moves; and a control device for receiving and processing the image signals fed from connected cameras.

It is recommended that two cameras are positioned at each side of face of patient to measure the relative three-dimensional movement of the movable marker in relation to the fixed marker.

The fixed marker has the shape of plate and a borderline with a specific color is provided at the edge of the fixed marker for the easy discrimination from the surroundings. The fixed marker has a corner point extraction marker formed on the borderline for the extraction of corner point which is needed to establish the fixed marker local coordinate system, and the corner point extraction marker has a different color from the borderline. Plurality of quadrangles are arrayed in a checkered pattern inside the borderline which is formed on the surface of the fixed marker, and the corner point is identified as the point where corners of quadrangles meet each other.

The movable marker has the shape of plate and smaller size than the fixed marker, and the movable marker has a borderline at the edge with a specific color for the easy discrimination from the surroundings. To obtain the corner point that is used as a data for the movement, plurality of quadrangles are arrayed in a checkered pattern on the surface of the movable marker. The movable marker has a corner point extraction marker with different color for the extraction of corner point, and the corner point extraction marker is identified as the pairs of quadrangles located in the four corners of the movable marker.

The coupling device is comprised of: a cross bar, a holding fixture, one end of which is anchored on the lower jaw of patient and the other end of which is connected to the mid-point of the cross bar in a manner that the other end of the holding fixture can make rotational movement in relation to the cross bar; a pair of translation frames connected to the both end of the cross bar in a manner that the translation frame can make translational and rotational movement in relation to the cross bar; and a measuring frame, one end of which is connected to the translation frame in a manner that the measuring frame can make a straight motion in the direction of orthogonal to the cross bar, and the other end of which is connected to the movable marker. The movable marker is removably connected to the other end of the measuring frame.

In place of the movable marker, a pointer may be alternatively connected to the other end of the measuring to represent the center of rotational motion of lower jaw of patient on the fixed marker or on the face of patient.

In addition, the present invention includes an orbital plane marker which is attached to a specific place around patient's eye to measure an orbitales(bottoms of the eye sockets), and the orbitales(bottoms of the eye sockets) is used to define the orbital plane.

The orbital plane marker has the shape of thin plate, and a borderline with a specific color is provided at the edge of the orbital plane marker for the easy discrimination from the surroundings. Four quadrangles are arrayed in a checkered pattern inside the borderline that is formed on the surface of the orbital plane marker, and the corner point of the orbital plane marker is identified as the point where corners of four quadrangles meet each other.

Meanwhile, the present invention provides the method of measuring the motion of jaw, which comprises the steps of: acquiring the image data through recording a fixed marker which is attached to the face of patient, and a movable marker which moves in unison with the motion of lower jaw with a camera; calculating the coordinate values of each corner point of the fixed marker and the movable marker according to the movement of lower jaw with the stereo vision processing of the acquired image data; calculating a coordinate transformation matrix between a fixed marker local coordinate system and a movable marker local coordinate system; calculating the location of hinge axis by using the coordinate values of the respective corner points at the before and after movement of the movable marker; and defining the left and right center of rotation of jaw motion by identifying the intersection point between the hinge axis and the fixed marker.

In concrete, the steps of calculating the location of hinge axis comprises the steps of: transforming the three-dimensional coordinate values of the movable marker before and after the translation movement of the movable marker; calculating the position vector and direction vector from the above calculated transformed coordinate values; and obtaining the linear equation of the line of the axis of hinge with respect to the the fixed marker local coordinate system.

The present invention includes the steps of: acquiring the image data by recording the orbital marker plane attached around the patient's eye with the camera, and calculating the coordinate value of the orbitales; and redefining the center of rotation with respect to the absolute coordinate system. An orbital plane is defined as a plane that includes the three points of said redefined left and right center of rotation and the orbitales.

In case of lower jaw makes both rotational and translational movement, the present invention includes the steps of: identifying the center of rotation as the fixed point on the movable marker; calculating the transformation matrix between fixed marker local coordinate system and the movable marker local coordinate system at any instant of the motion of lower jaw; transforming the coordinate value of center of rotation, defined with respect to the movable marker local coordinate system, into the coordinate values of fixed marker local coordinate system; and tracing the track the center of rotation with respect to the orbital plane.

BRIEF DESCRIPTION OF THE DRAWINGS

These and other objects of the present invention will become more readily appreciated and understood from a consideration of the following detailed description of the preferred embodiment when taken together with the accompanying drawings, in which:

FIG. 1 is a schematic view of jaw motion measuring apparatus of the present invention;

FIG. 2 is a side view of the apparatus according to FIG. 1;

FIG. 3 is a front view of the fixed marker of the apparatus according to FIG. 1;

FIG. 4 is a front view of the movable marker of the apparatus according to FIG. 1;

FIG. 5 is a front view of the orbital plane marker of the apparatus according to FIG. 1;

FIG. 6 is a flow chart of the jaw motion measuring method when the motion of patient's lower jaw is small showing only rotational motion;

FIG. 7 is a schematic view of the rotation and translation of the fixed marker local coordinate system and movable marker local coordinate system with respect to the camera coordinate system;

FIG. 8 is a schematic view of the relationship between the absolute coordinate system and the fixed marker local coordinate system;

FIG. 9 is a schematic view of orbital plane defined with respect to the absolute coordinate system;

FIG. 10 is a flow chart of the jaw motion measuring method when the patient's lower jaw makes both rotational and translational motion;

FIG. 11A is a perspective view of the state when fixed marker is detached from the measuring apparatus; and FIG. 11B is a perspective view of the state when pointer is connected to the measuring apparatus of FIG. 1 where fixed marker is removed.

DETAILED DESCRIPTION OF PREFERRED EMBODIMENTS

Hereinafter, the preferred embodiment of the present invention will be described in greater detail with reference to the accompanying drawings.

FIG. 1 is a schematic view of jaw motion measuring apparatus of the present invention.

As illustrated in FIG. 1, jaw motion measuring apparatus according to present invention comprises a pair of fixed marker 10, 10' attached to both sides of face of patient; two movable marker 20, 20' disposed to face the fixed marker in a spaced distance and to move in unison with the movement of the lower jaw of patient; four cameras 30 recording the relative movement of the movable marker in relation to the fixed marker, as lower jaw moves; and personal computer 40 for receiving and processing the image signals fed from connected cameras.

Movable marker 20, 20' is connected to holding fixture mounted on the lower jaw of patient, through cross bar 53, translation frame 55 and measuring frame 57 so as to move in unison with the movement of lower jaw of patient.

One end of the holding fixture 51 is anchored on the lower jaw of patient and the other end the holding fixture 51 is connected to the mid-point of cross bar 53 in a manner that the other end of the holding fixture can make rotational and translational movement in relation to the cross bar 53. Translation frame 55 is connected to the both end of the cross bar 53 in a manner that the translation frame 55 can make translational and rotational movement in relation to the cross bar 53. Movable marker 20, 20' is removably attached to the measuring frame. One end of measuring frame 57 is connected to the translation frame 55 in a manner that the measuring frame can make a straight motion in the direction of orthogonal to the cross bar 53.

The position of movable marker 20, 20' is adjusted to face fixed marker 10, 10' within the view range of camera by making rotational or translational movement of holding fixture 51 and translation frame 55 on cross bar 53 and by making translational movement of measuring frame 57 on translation frame 55 according to the skull size of patient.

Reference number 100 denotes the three-dimensional absolute coordinate system, and reference number 110, 120, 130, 140 denotes the respective three-dimensional location coordinate system of four cameras. Reference number 150, 170 denotes the respective local coordinate system of a pair of fixed marker 10, 10', and reference number 160, 180 denotes the respective local coordinate system of a pair of movable marker 20, 20'.

FIG. 2 is a side view of the apparatus according to present invention is mounted on the head of patient.

As illustrated in FIG. 2, fixed marker 10, 10' is attached to the most probable center of rotation of jaw within the view range of camera. Reference number 60 denotes the orbital plane marker. Orbital plane marker 60, along with fixed marker 10, is attached to a specific location around the patient's eye, e.g. orbitales(bottoms of the eye sockets). Together with the center of rotation of jaw, orbital plane marker 60 defines orbital plane as explained below, and suffices if it is attached to any one side of patient's face.

For the process of Stereo Vision Processing, four cameras—two at each side of patient's face—are installed to practice focusing on fixed marker 10, 10', movable marker 20, 20' and orbital plane marker 60. While CCD(Charge Control Device) camera or CMOS(Complementary Metal-Oxide Semiconductor) camera, which is used for personal computer in general, is recommended, infrared camera can be used instead.

FIG. 3 is drawing that illustrates a front view of the fixed marker 10, 10', or the plane facing toward camera 30. Fixed marker 10, 10' is for the establishment of coordinate system 150, 170, which plays role as the basis coordinate system for the relative local coordinate system of movable marker 20, 20'.

As illustrated in FIG. 3 fixed marker 10 assumes the shape of square plate. Fixed marker 10 has a borderline 11 of specific color(e.g. blue), at the edge. The borderline 11 is for the discrimination between the interior and the exterior of the fixed marker 10. In the concrete, the borderline 11 plays a role as the boundary that eliminates the unnecessary signals form the signals obtained from camera 30 except the signals from the interior area of the fixed marker 10.

Inside the borderline 11, white and black quadrangles are arrayed in checkered pattern so as to establish the fixed marker local coordinate system precisely. In other words, the coordinate value of the meeting point of the quadrangles (hereafter termed as "corner point") is used to establish fixed marker 150, 170.

Near the three corners of the borderline 11 are formed three pairs of corner point extraction markers 12, 13, 14, two at each corner area. The corner point extraction markers 12, 13, 14, which assume different colors(e.g. red, green, yellow)to be identified from one another, are used to extract the basis corner point 16. The basis corner point 16, which is located near the corner point extraction marker 12, 13, 14, is the reference point for calculating all the corner points of fixed marker 10. When the basis corner point 16 is known, every corner points can be extracted based on the basis corner point 16 thus enabling the establishment of fixed marker local coordinate system 150, 170.

FIG. 4 shows the front view of the movable marker, that is, the facing plane of camera 30.

As illustrated in FIG. 4, the size of the movable marker 20 is smaller than fixed marker 10, and the movable marker 20 has the shape of rectangular plate. The movable marker 20 has two adjacent borderline, exterior borderline 21 and interior borderline 22, at the edge, which has different colors(e.g. red and black). Inside the exterior borderline 21 and interior borderline 22 of the movable marker 20 are formed plurality of quadrangles in a checkered pattern to obtain corner points which is used as a basis point for establishing movable marker 20 and the data for the movement of movable marker 160, 180. Exterior borderline 21 and interior borderline 22 play roles as a boundary, which is used to eliminate the image signals other than the signals from the checkered part.

Each of the two quadrangles located at the four corners of movable marker 20, is used as the corner point extraction marker 23, 24, 25, 26. The corner point extraction marker 23, 24, 25, 26 play a role as a indicator for finding four basis corner point 28 which is used to extract corner point of movable marker 20. The corner point extraction marker 23, 24, 25, 26 assume four colors that are different from the colors of the exterior borderline 21 and interior borderline 22(e.g. red, green, blue, yellow). Basis corner point 28 is identified as the meeting points of the corner of a pair of quadrangles which comprise the corner point extraction marker 23, 24, 25, 26, that is, the points where the corners of four quadrangles, located at the corner area of movable marker 20, meet each other.

The other quadrangles, except those that comprise corner point extraction marker 23, 24, 25, 26, is arrayed in checkered pattern with alteration of two different colors(e.g. white and black). The corner point of the movable marker 20 is the position where the corner of the quadrangles meet each other.

FIG. 5 shows the front view of orbital plane marker, that is, the facing plane of camera 30.

As shown in FIG. 5, the size of orbital plane marker 60 is smaller than movable marker 20, and the orbital plane marker 20 has the shape of rectangular plate. Orbital plane marker 60 has specific color of borderline 61(e.g. blue), at the edge. Inside of the borderline 61 of orbital plane 60 are arrayed quadrangles with two different colors in a checkered pattern (e.g. white and red). Borderline 61 is used to discriminate between the checkered part and the other part, thus eliminating the unnecessary signals other than the signals from the checkered part.

The corner point extraction marker 62 of the orbital plane marker 60 is identified as the diagonally positioned two quadrangles of the four quadrangles arrayed in checkered pattern. Corner point extraction marker 62 plays a role as a indicator for the direct extraction of corner point such as the specific point of orbitales(bottoms of eye socket), and the corner point assumes different color from the colors of borderline 61 and the rest quadrangles. The corner point P of the orbital plane marker 60 is identified as the meeting point of the corners of four quadrangles that are arrayed in checked pattern.

While this preferred embodiment explains the method of defining orbital plane by measuring orbitales(bottoms of eye socket), other methods of defining orbital plane like directly recognizing specific point e.g. the tip point of eye socket with camera 30 and identifying the position with the orbitales(bottoms of eye socket) can be possible.

Hereafter is explained the method of determining the center of rotation of the motion of patient's jaw and defining the Orbital Plane by measuring the motion of patient's jaw.

In this present invention, holding fixture 51, cross bar 53, translation frame 55 and measuring frame 57 to which movable marker 20, 20' is installed, can be regarded as one rigid body, and above the components make motions as the lower jaw of patient makes motions. As movable marker 20 moves in unison with patient's lower jaw, movable marker 20, 20' makes a relative movement in relation to the fixed marker attached to the both sides of patient's face. The relative movement can be measured with four cameras 30 through recording the relative movement of the corner point of movable marker 20, 20' in relation to the corner point of fixed marker 10, 10', and stereo-vision processing the image data with computer 40.

FIG. 6 is a flow chart of the jaw motion measuring method when the motion of patient's lower jaw is so small that shows only rotational motion. The object of the method according to FIG. 6 is to define the center of rotation of patient's motion on the fixed marker 10, 10' and to establish the orbital plane with respect to the absolute coordinate system 100. In case the motion of patient's lower jaw is so small and shows only rotational motion, the measuring process of the patient's jaw is accomplished by the process as explained below.

In the first place, obtain the image data of the fixed marker 10, 10', movable marker 20, 20', orbital plane marker 60 with four cameras 30 while the patient's lower jaw makes a motion(S11), and calculate the respective three-dimensional coordinate value of the corner points of the the markers 10, 10', 20, 20', 60(S12). The three-dimensional coordinate values of the corner points is defined with respect to the local coordinate system 110, 140 of the two cameras, which is located at the both sides of patient's face, for example the ones that are located in left lower and right lower position in the FIG. 1.

Then, calculate the coordinate transformation matrix between fixed marker local coordinate system 150, 170 and the movable marker local coordinate system 160, 180, using the three-dimensional coordinate values of the fixed marker 10, 10' and movable marker 20, 20' with computer 40(S13). For example, In case of the left positioned fixed marker 10 and movable marker 20 in FIG. 1, coordinate transformation matrix, which shows the amount of rotation or translation of the fixed marker local coordinate system 150 and movable marker local coordinate system 160 with respect to the location coordinate system 110 of the left-lower positioned camera, can be calculated as illustrated in FIG. 7.

Then, calculate the hinge-axis according to the movement of movable marker 20, 20' using the coordinate values of the before and after movement of movable marker 20, 20'(S14). And then calculate the center of rotation of lower jaw movement, i.e. the left and right Hinge Point of jaw from the hinge-axis derived form above process(S15)

The detailed explanations of the process of calculating the Hinge Points according to process S14 and S15 are as follows. As illustrated above, the fixed marker local coordinate system can be established by using three-dimensional coordinate values of the corner point of the fixed marker 10. 10'. The respective fixed marker local coordinate system 150, 170 is defined with respect to the absolute coordinate system as illustrated in FIG. 8. The center of motion of lower jaw(i.e. Hinge Point) can be obtained in reference to the fixed marker local coordinate system 150, 170. In the first place, the three-dimensional coordinate values of the before and movement of the corner point of movable marker 20, 20' are transformed into the values of the fixed marker local coordinate system 150, 170. Then, calculate the position vector and direction vector of the Hinge Axis using the Screw Theory. When the position vector and direction vector of the Hinge Axis is obtained, the linear equation of the Hinge Axis with respect to the fixed marker local coordinate system, can be calculated. And then, the center of rotation of lower jaw(C1, C2) is identified as the intersection point of the linear equation of Hinge Axis and the x-y plane of the fixed marker local coordinate system 150, 170 (i.e. the surface of the fixed marker 10, 10').

The center of rotation of lower jaw(C1, C2) obtained at S15 is the value that is defined in respective fixed marker local coordinate system 150, 170. After S15, the center of rotation of lower jaw is re-defined with respect to the absolute coordinate system 100(S16). Then, define the orbital plane by using the left and right center of rotation of lower jaw(C1, C2) and the specific point like obitales (bottoms of the eye socket) which has been measured with the orbital plane marker 60(S17). The orbital plane is defined as the plane which includes the three points of the left and right center of rotation of lower jaw(C1, C2) and the obitales(bottoms of the eye socket) as illustrated in FIG. 9. In FIG. 9, reference number 190 denotes the local coordinate system of orbital plane.

Meanwhile, translational movement as well as rotational movement occurs when the motion of lower jaw is large, thus making it necessary to trace the track of the movement of center of rotation of jaw.

The present invention re-define the left and right center of rotation of lower jaw(C1, C2) with respect to movable marker local coordinate system 160, 180, which has been defined with respect to fixed marker local coordinate system 150,170 for the tracing of the track of center of rotation of lower jaw, as illustrated in FIG. 6. In other words, if the center of rotation of lower jaw(C1, C2), which has been acquired from the method of FIG. 6, is set up as the permanently fixed point in the movable marker local coordinate system 160, 180, the coordinate value of center of rotation of lower jaw(C1, C2) remains as a fixed point, but with respect to the fixed marker local coordinate system 150, 170, the center of rotation of lower jaw(C1, C2) keeps changing as the lower jaw keeps moving. The transformation matrix between the fixed marker local coordinate system 150, 170 and the movable marker local coordinate system 160, 180 at the every instant of the movement of lower jaw can be calculated. As a result, the tracking of the center of rotation of lower jaw(C1, C2) with respect to the fixed marker local coordinate system 160, 170 is made possible, by transforming the coordinate value of the center of rotation of lower jaw(C1, C2) with respect to movable marker local coordinate system into the correspondent coordinate value with respect to the fixed marker local coordinate system.

In addition, the track of motion with respect to the fixed marker can be transformed into the correspondent track of motion with respect to the orbital plane coordinate system, as the transformation relationship between the above two coordinate system can be calculated. That is, the moving track of center of rotation of lower jaw(C1, C2) can be measured with respect to orbital plane, which has been defined in FIG. 6.

FIG. 10 is a flow chart of the jaw motion measuring method when the patient's lower jaw motion is so large that it makes both rotational and translational motion In the first place, obtain the image data of the fixed marker 10. 10', and movable marker 20, 20' at the every instant of motion(S21), and calculate the three-dimensional coordinate value of the respective corner points of the fixed marker 10, 10' and movable marker 20. 20' through stereo-vision processing the above obtained image data with computer 40(S22). And then, calculate the transformation matrix between the fixed marker 10, 10' and movable marker 20, 20'(S23).

Then, by using the transformation matrix obtained in S23, transform the coordinate value of the center of rotation of lower jaw(C1, C2) with respect to movable marker local coordinate system 160, 180, into the correspondent value with respect to the fixed marker local coordinate system 150, 170(S24). The value of the center of rotation of lower jaw(C1, C2) with respect to the fixed marker local coordinate system 150, 170 keeps changing, and hereafter, the the changing coordinate value is termed as "virtual center of rotation".

Finally, the virtual center of rotation at the every instant of jaw motion is stored in computer(S25), and the moving track can be displayed in the computer monitor by the output format of graph.

Meanwhile, the center of rotation of jaw motion and it's moving track should be marked on the surface of fixed marker 10, 10' and the side part of patient's face, and this method is illustrated in FIG. 11A and FIG. 11B.

As illustrated in FIG. 11A, movable marker 20, 20' is installed at the front end of measuring frame 57 in a removably attachable manner. Movable marker 20, 20' is removed from the measuring frame, after being used in the acquisition of the center of rotation of patient's jaw. Then, as illustrated in FIG. 11B, pointer 80 is installed on the front end of measuring frame in place of the removed movable marker 20, 20'. The tip of the pointer 80 is provided with colored liquid like ink, so as to mark the center of rotation of lower jaw(C1, C2) on the surface of fixed marker 10, 10'.

The location of pointer 80 can be monitored in the computer 30 monitor through camera 30. The user can mark the center of rotation of lower jaw(C1, C2) on the surface of fixed marker 10, 10' while adjusting the location of pointer 80 by letting the translation frame 55 and measuring frame 57 make translational and rotational motion, and the whole process can be monitored in the computer monitor.

Meanwhile, to mark the center of rotation of lower jaw(C1, C2) directly on the patient's face, the fixed marker 10, 10' is removed and the pointer 80 is moved toward the patient's face to the extent that fixed marker 10, 10' contacts the patient's face.

According to present invention, as illustrated above, this invention can reduce the pains that resulted form the long measuring time of the previous hand-operated apparatus, and this invention, also, improves the degree of reproducibility.

In addition, the present invention can reduce the measuring cost of the jaw movement, as it employs cheap personal computer in comparison with the previous automated measuring apparatus that employs expensive devices, like infrared sensor.

In addition, the present invention can be adapted to the occlusion simulation with CAD technology, as this invention can define the Orbital Plane easily. Also, the present invention can provide a jaw motion measuring apparatus that can directly mark the center of the motion of jaw on the surface of patient's face, thus being applicable to the conventional diagnosis of occlusion and dental treatment using occlusion device and plaster.

The forgoing embodiment is merely exemplary and is not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. An apparatus for measuring the center of rotation of jaw motion and the track thereof, the apparatus comprising:
    a pair of fixed markers attached to the left side and right side of patient's face respectively;
    a pair of movable markers disposed to face the fixed markers in a spaced distance and moving in unison with the movement of the lower jaw of patient;
    a coupling device for connecting the movable markers to the lower jaw of patient;
    a plurality of cameras for recording the movement of the movable markers relative to the fixed markers, according to the movement of lower jaw; and
    a control device for receiving and processing the image signals fed from connected cameras,
    wherein the fixed markers have the shape of a plate, and a borderline with a specific color is provided at the edge of each fixed marker for the easy discrimination from the surroundings, and a plurality of quadrangles are arrayed in a checkered pattern inside the borderline which is formed on the surface of the fixed markers.

2. The apparatus of claim 1, wherein two cameras are positioned at each side of patient's face to measure the three-dimensional movement of a respective movable marker relative to a respective fixed marker.

3. The apparatus of claim 1, wherein the fixed markers each have a corner point extraction marker formed on the borderline for the extraction of corner point which is needed to establish the fixed marker local coordinate system, and the corner point extraction marker has a different color from the borderline.

4. The apparatus of claim 1, wherein the movable markers have the shape of a plate and a smaller size than the fixed markers, and each movable marker has a borderline at the edge with a specific color for the easy discrimination from the surroundings.

5. The apparatus of claim 4, wherein a plurality of quadrangles are arrayed in a checkered pattern on the surface of each movable marker, and each movable marker has the shape of a quadrangular plate.

6. The apparatus of claim 5, wherein each movable marker has a corner point extraction marker with a different color for the extraction of corner point which is needed to establish the movable marker local coordinate system, and the corner point extraction marker is identified as the pairs of quadrangles located in the four corners of the movable marker.

7. The apparatus of claim 1, wherein the coupling device comprises:
    a cross bar;
    a holding fixture, one end of which is anchored on the lower jaw of patient and the other end of which is rotatably connected to the mid-point of the cross bar;
    a pair of translation frames connected to the both ends of the cross bar in a manner that the translation frame can make translational and rotational movement; and
    a pair of measuring frames, at least one of the measuring frames having one end connected to the translation frame in a manner that the measuring frame can make a straight motion in the orthogonal direction to the cross bar, and the other end connected to one of the movable markers.

8. The apparatus of claim 7, wherein said one movable marker is removably connected to the other end of the measuring frame.

9. The apparatus of claim 8, further comprising a pointer alternatively connectable to the other end of the measuring frame in place of a moveable marker to represent the center of rotation of lower jaw of patient on the surface of a respective fixed marker or the face of patient.

10. The apparatus of claim 1, further comprising a pointer to represent the center of rotation of lower jaw of patient on the surface of each fixed marker or the face of patient, wherein the pointer is alternatively attachable to the coupling device in place of at least one of the movable markers.

11. The apparatus of claim 1, wherein the control device is a personal computer.

12. The apparatus of claim 1, further comprising an orbital plane marker attached to a specific location around patient's eye to measure an orbitales, and the orbitales is used to define the orbital plane.

13. The apparatus of claim 12, wherein the orbital plane marker has the shape of a thin plate, and a borderline with a specific color is provided at the edge of the orbital plane marker for the easy discrimination from the surroundings.

14. The apparatus of claim 12, wherein four quadrangles are arrayed in a checkered pattern inside the borderline of the orbital plane marker, and the corner point of the orbital plane marker is identified as the point where corners of four quadrangles meet each other.

* * * * *